(12) United States Patent
 Agrawal

(10) Patent No.: US 8,608,692 B2
(45) Date of Patent: Dec. 17, 2013

(54) FLUID COLLECTION SELF-LOCKING, SELF-BLUNTING SAFETY NEEDLE SYSTEM AND SYRINGE

(76) Inventor: Arpita Agrawal, Chicago, IL (US)

( * ) Notice: Subject to any disclaimer, the term of this patent is extended or adjusted under 35 U.S.C. 154(b) by 262 days.

(21) Appl. No.: 12/450,262

(22) PCT Filed: Mar. 20, 2008

(86) PCT No.: PCT/US2008/003647
§ 371 (c)(1),
(2), (4) Date: Sep. 17, 2009

(87) PCT Pub. No.: WO2008/118330
PCT Pub. Date: Oct. 2, 2008

(65) Prior Publication Data
US 2010/0036316 A1    Feb. 11, 2010

Related U.S. Application Data

(60) Provisional application No. 60/919,454, filed on Mar. 22, 2007.

(51) Int. Cl.
*A61M 5/00* (2006.01)
(52) U.S. Cl.
USPC ........................................... 604/110
(58) Field of Classification Search
USPC ............... 604/110, 164.01, 164.08, 604/165.01–165.03, 170.01, 170.02, 239, 604/263, 272; 600/562, 566, 567, 583; 606/167, 181, 184
See application file for complete search history.

(56) References Cited

U.S. PATENT DOCUMENTS

| | | | |
|---|---|---|---|
| 3,478,937 A | 11/1969 | Solowey | |
| 3,885,562 A * | 5/1975 | Lampkin | ........................ 604/189 |
| 3,982,546 A | 9/1976 | Friend | |
| 4,233,975 A | 11/1980 | Yerman | |
| 4,828,547 A * | 5/1989 | Sahi et al. | ...................... 604/110 |
| 4,892,107 A | 1/1990 | Haber | |
| 5,423,760 A | 6/1995 | Yoon | |
| 5,993,418 A | 11/1999 | Alexander | |
| 6,733,465 B1 | 5/2004 | Smutney et al. | |
| 6,814,707 B2 | 11/2004 | Collins et al. | |
| 2003/0093038 A1 | 5/2003 | Chiang | |
| 2005/0027263 A1 | 2/2005 | Woehr et al. | |
| 2007/0016142 A1 | 1/2007 | Burren et al. | |

FOREIGN PATENT DOCUMENTS

WO    WO 2007027507 A2 *    3/2007

OTHER PUBLICATIONS

U.S. Appl. No. 11/991,114, filed Mar. 8, 2007, Agrawal.

* cited by examiner

*Primary Examiner* — Nicholas Lucchesi
*Assistant Examiner* — Nathan R Price

(57) ABSTRACT

The invention is related to a particular type of safety needle and syringe. The needle has a locking device which can be used with or without a syringe. The needle is cylindrical with one surface flattened out. The Blunting member is aligned within the needle. With the intake of fluids the blunting instrument moves out, blocks the needle tip and locks inside the needle. Thus preventing reuse and needle stick Injury.

20 Claims, 16 Drawing Sheets

FLUID COLLECTION SELF-LOCKING, SELF-BLUNTING SAFETY NEEDLE SYSTEM AND SYRINGE

CROSS-REFERENCE TO RELATED APPLICATIONS

This is a Section 371 National Stage application based on PCT International Application No. PCT/US08/03647, filed on Mar. 20, 2008, claiming priority from U.S. Provisional Patent Application No. 60/919,454 filed on Mar. 22, 2007.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC

Not applicable.

BACKGROUND OF INVENTION

1. Field of the Invention

The present invention relates to a safety needle system and syringe. The safety needle system may be used with a hypodermic syringe, IV Catheter, and for every other medical or industrial purpose. The invention is also broadly applicable to needles connected to fluid transfer devices other than syringes, and applications in medical and non-medical use. The needle is a self blunting instrument which after intake of fluid prevents needle stick injuries.

The needle is safe during and after use, the safety feature being an integral part of the design. The intention is to create a simple low cost self blunting needle system and syringe which does not require human action to activate the safety feature.

The invention requires no additional learning or training by the medical or non-medical staff for the blunting of the needle.

2. Description of Related Art

Syringes have been designed to prevent reuse or have automatic or mechanical safety features. U.S. Pat. No. 4,233,975 discloses a syringe in which a plug is positioned in the syringe to be pushed into a position of blocking flow to and from the syringe needle passage.

U.S. Pat. No. 3,478,937 discloses a syringe in which the plunger stem 23 has a collar unit 25 secured thereon which, when the plunger is pushed through the barrel 11 of the hypodermic syringe, it passes through ring 26 mounted at one end of the barrel to prevent subsequent retraction of the plunger for refuse of the device.

US Pat No. 2005/0027263 for an IV Catheter includes a unitary, resilient needle guard received in a catheter hub. The needle guard includes a proximal arm or wall that includes an opening through which a needle passes for axial movement. When the needle is retracted from the catheter, it releases the force that had previously prevented movement of the needle guard within into a position in which it is clamped onto the needle shaft and in which its distal wall blocks access to the needle tip. In the condition, the spring needle guard and needle can be removed from the catheter hub. A slot or crimp may be formed in the needle shaft that engages with the needle guard after the protected needle and needle guard are removed from the catheter hub, thereby to prevent removal of the protected needle from the needle guard.

U.S. Pat. No. 6,814,707 discloses a blood collection device which includes a syringe assembly containing a slidable needle assembly within the cavity of a syringe body. The invention retracts the needle within a disposable syringe.

US Patent Application Publication No. US 2003/0093038 discloses a needle retraction type safety syringe in which the passive needle retraction element after engaging with the active needle retraction element can be forced to separate from the positioning restriction of the second positioning means that the needle can be retracted into the barrel by pulling back the push rod.

U.S. Pat. No. 4,892,107 discloses a single use safety blood collection device, which permits retraction of the hypodermic needle after its use into the sleeve of the device, itself to thereby to encapsulate the used needle. Once the needle is retracted after use it cannot thereafter be extended again.

BRIEF SUMMARY OF THE INVENTION

In a first separate aspect, the present invention is a device that makes the use of, syringes and needles safe during and after use, while in-taking fluids.

In a second separate aspect, the safety feature being an integral part of the invention is activated with routine use of the product. The self blunting needle system and syringe does not require human action to activate the safety feature, thus reducing chances of error.

In a third separate aspect, as the safety feature does not require additional action to activate, this eliminates the learning curve for the use of the product.

In a fourth separate aspect, the changes and modifications to the syringe are made to create a simple low cost self blunting needle system and syringe.

The foregoing and other objectives, features and advantages of the invention will be more readily understood upon consideration of the following detailed description taken in conjugation with the accompanying drawings.

BRIEF DESCRIPTION OF THE SEVERAL VIEWS OF THE DRAWING(S)

The invention can be better understood with reference to the following drawings. The elements of the drawing are not necessarily to scale relative to each other, emphasis instead being placed upon clearly illustrating the principles of invention.

DRAWING—REFERENCE NUMERALS

- 101—Hypodermic syringe
- 102—Syringe tube
- 103—Flattened surface along syringe tube
- 104—Plunger rod
- 105—Normal plunger arm
- 106—Flattened plunger arm
- 107—Thumb rest
- 108—Plunger head support
- 109—Cavity between plunger arms and plunger head
- 110—Plunger head
- 111—Plunger head flattened surface
- 112—Plunger head extension
- 113—Syringe cavity
- 114—Syringe depression
- 115—Fulcrum point
- 116—Syringe head
- 117—Syringe head flattened surface
- 118—Needle generally
- 119—Needle mouth
- 120—Needle mouth flattened surface
- 121—Needle tube
- 122—Needle cavity
- 123—Needle tube flattened surface
- 124—Needle opening
- 125—Needle curvature
- 126—Needle puncture tip
- 127—Needle tip angle
- 128—Needle mouth and needle tube touch
- 129—Blunting member stopper
- 130—Alternate blunting member stopper
- 131—Moving member
- 132—Blunting member
- 133—Blunting member cavity
- 134—Blunting member flattened surface
- 135—Blunting member curvature
- 136—First indent
- 137—Sheathing indent
- 138—Puncture tip protector
- 139—Moving member blunting member edge
- 140—Moving member plunger head edge
- 141—Plunger head extension guide
- 142—Moving member stopper
- 143—Blunting member guide
- 144—Moving member incline lower part
- 145—Moving member incline higher part
- 146—Releasing joint releasing part
- 147—Releasing joint released part
- 148—Fulcrum point stopper
- 149—Fulcrum point incline
- 150—Fulcrum point released part
- 151—Moving member fulcrum joint
- 152—Moving member extension
- 153—Non releasing plunger head extension guide
- 154—Blunting member thickness variation
- 155—Blunting member outward indent
- 156—Blunting member transition in shape
- 157—Multiple blunting members

DETAILED DESCRIPTION OF THE INVENTION

Figure 2:
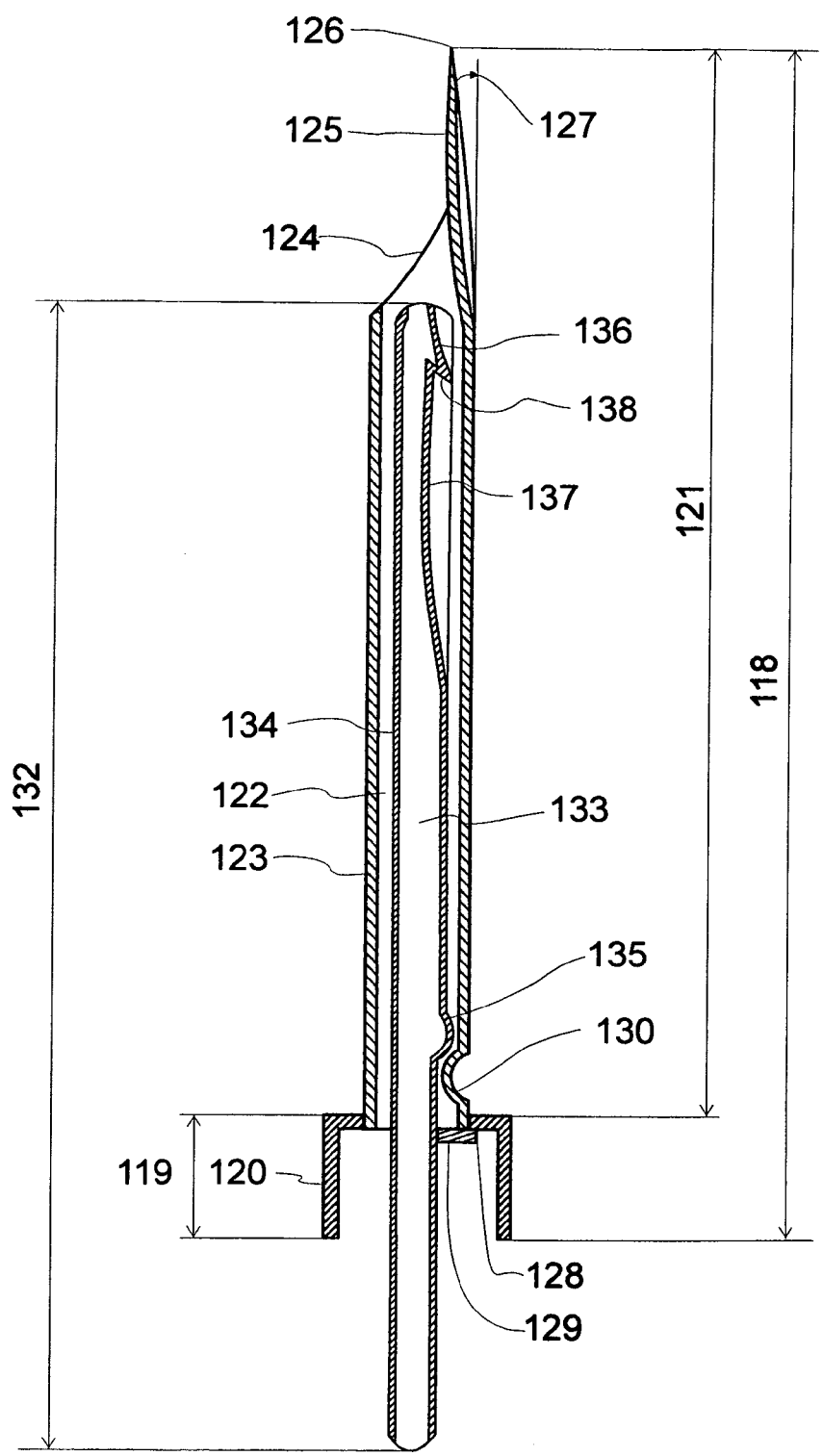
FIG. 2 is a cross section view of the needle and blunting member.

The invention comprises of the following components; FIG. 2 shows a needle member 118 which terminates in a needle puncture tip 126. The needle member 118 has a slight inward or outward curvature 125 before it tapers into the needle puncture tip 126. This inward or outward curvature 125 will lock the blunting member 132 in the extended position. Furthermore, the needle puncture tip 126 will be at an acute angle 127 to facilitate the sheathing of the needle puncture tip 126. The needle member 118 has a stopper 130 to prevent the blunting member 132 from falling out of the needle mouth 119. The stopper on the needle member 130 is placed on the needle tube member 121 or alternately at the point where the needle tube 121 and needle mouth 119 meet at 128.

Figure 1:
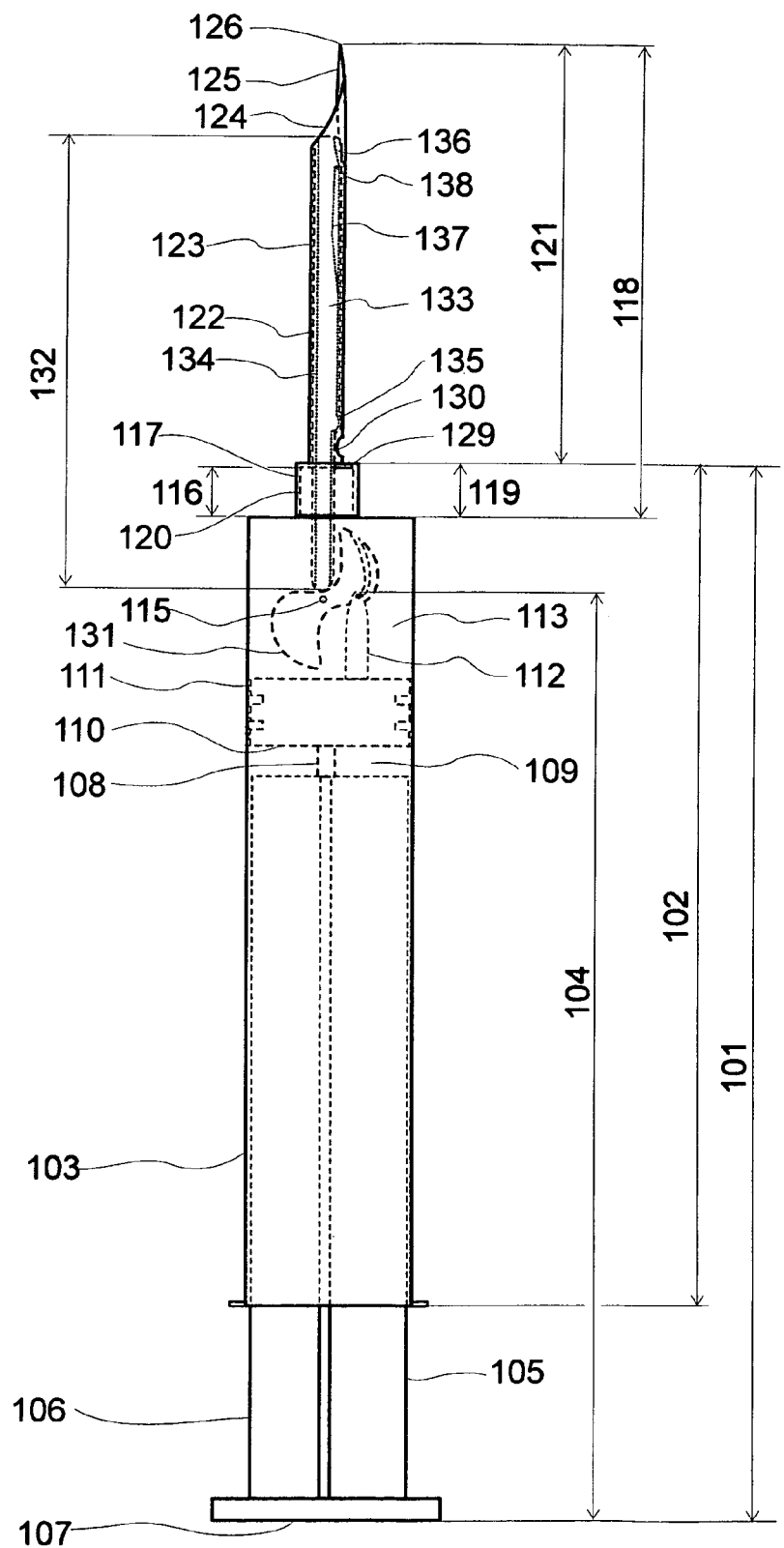
FIG. 1 is a complete view of the hypodermic syringe with needle, at shipping position.
Figure 4:
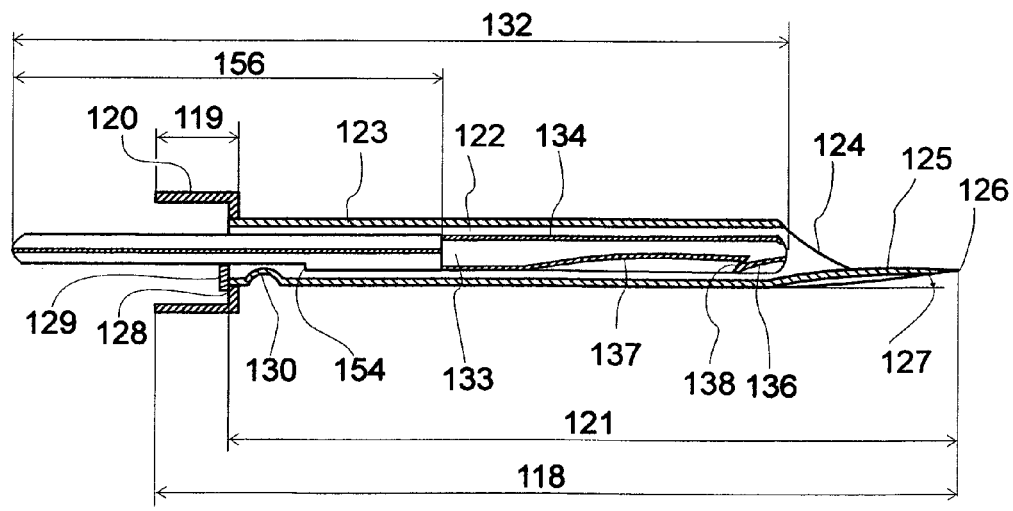
FIG. 4 shows blunting member with varying thickness and transition of shape.
Figure 8:
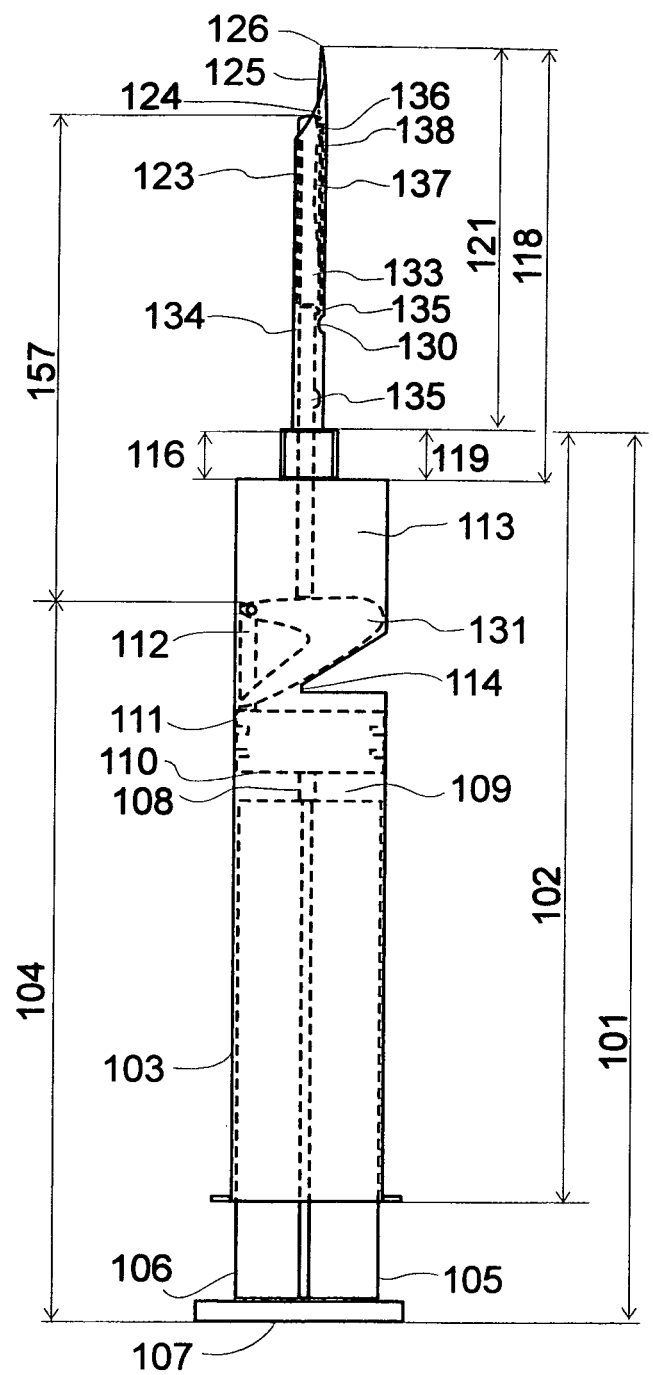
FIG. 8 is a view of the hypodermic syringe with needle with the moving member not attached to fulcrum point, at shipping position.
Figure 9:
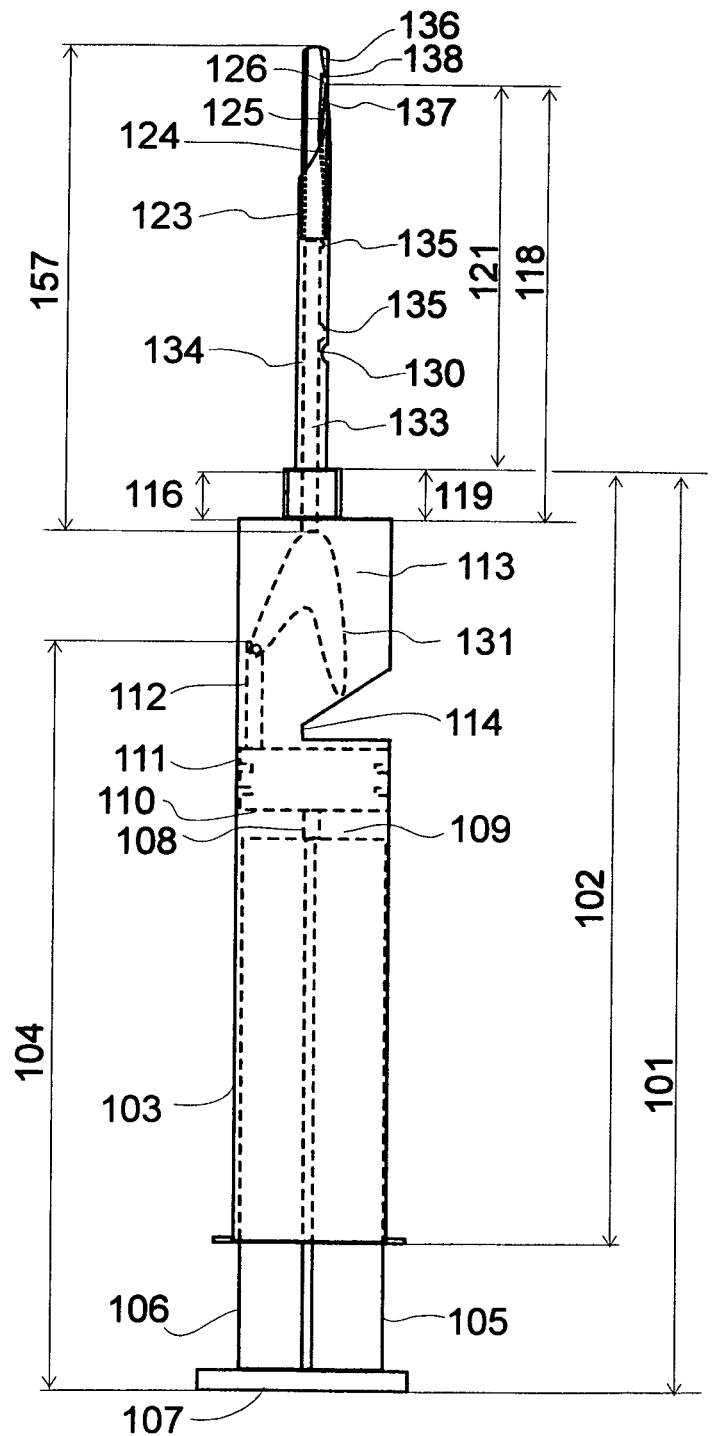
FIG. 9 is a view of the hypodermic syringe with needle with the moving member not attached to fulcrum point, during withdrawal of fluids.

A blunting member 132 is placed inside the needle member 118. Blunting member 132 may extend outside the needle mouth 119 into the syringe tube 102 or one of the parts of the blunting member 132 can extend outside the needle mouth 119 into the syringe tube 102 to be pushed by the moving member 131 or the moving member 131 can have an extension going into the needle tube 121 to push the blunting member 132, as shown in FIG. 1. The blunting member 132 can be of any shape as long as it aligns within the needle 118, allows for the flow of fluids and locks. The blunting member 132 can comprise of a single part or be divided into multiple parts 157 as shown in FIG. 8 and FIG. 9. The blunting member 132 has a curvature 130 that stops the blunting member 132 or its multiple parts 157 from falling out through the needle mouth 119, when it is stopped by a stopper 130 on the needle member. Alternately to the blunting member curvature 130 the blunting member 132 can have variation in thickness 154, where the thicker part gets stopped at the blunting member stopper 129 or alternate blunting member stopper 130 on the needle member 118 as shown in FIG. 4.

Figure 12:
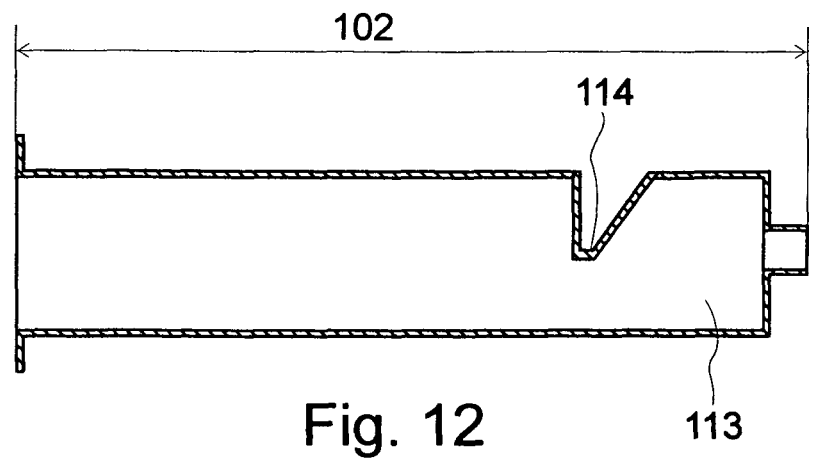
FIG. 12 is the cross section view of the syringe depression.

FIG. 12 shows that the syringe tube 102 has a syringe depression 114. This raised member 114 inside the syringe tube 102 is independently or in combination means of providing a fulcrum point 115, guide movement of moving member 131 and stop movement of moving member 131 in one direction.

Figure 7:
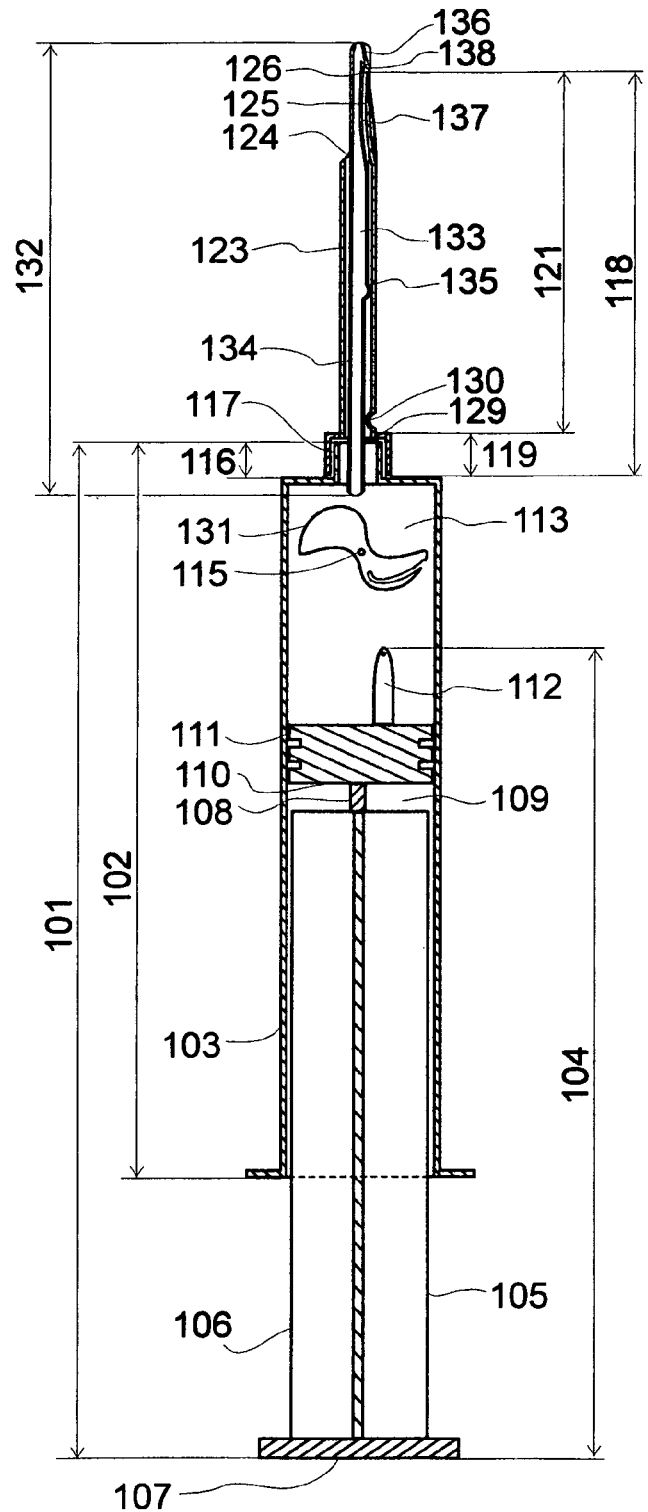
FIG. 7 is the cross section view of the hypodermic syringe and needle after use.

Fulcrum point 115 on the syringe depression 114 provides a pivot point for the moving member 131. Fulcrum point 115 also stops movement of the moving member 131 in one direction. Fulcrum point 115 has a snap fit to provide ease of assembly to the moving member 131. Moving member 131 stays attached to the fulcrum point 115 or alternately the fulcrum point 115 allows the release of the moving member 131 after pushing the blunting member 132 further into the needle tube 121 to sheath the needle puncture tip 126 as shown in FIG. 7.

Figure 6:
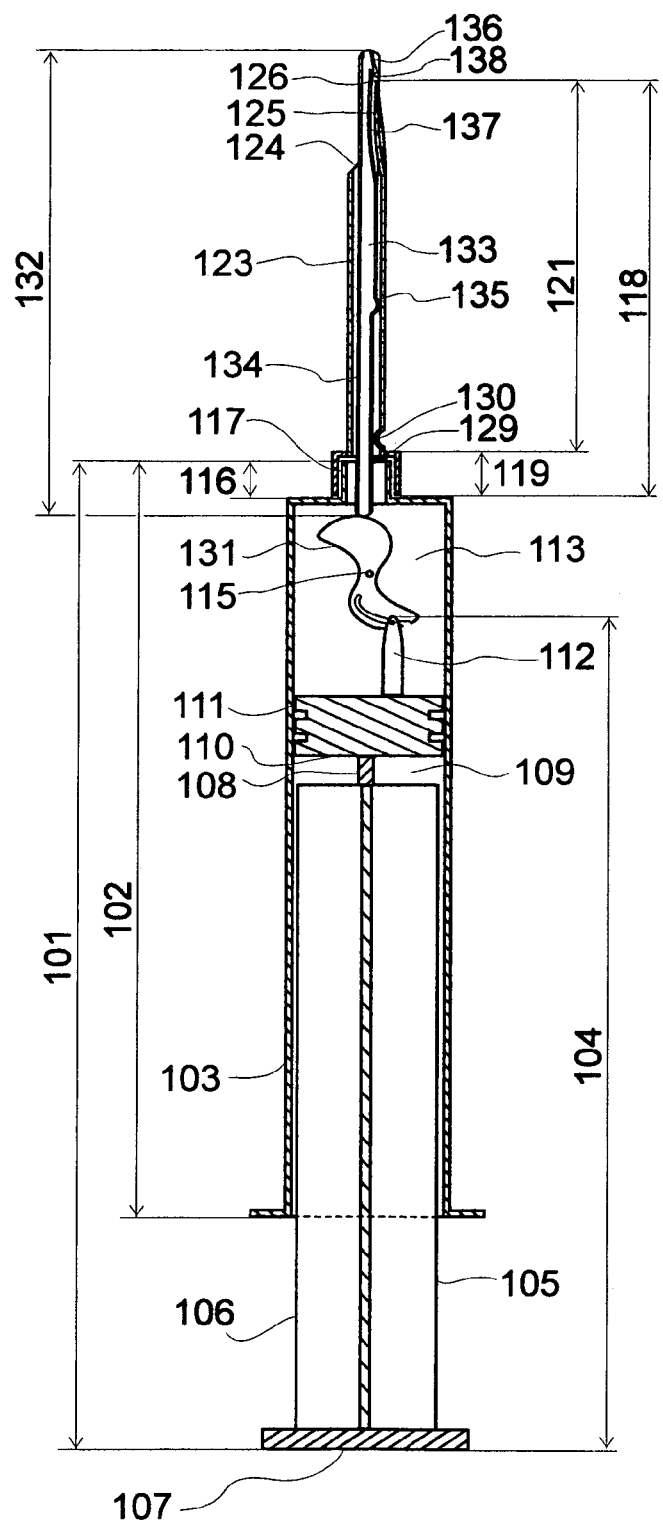
FIG. 6 is the cross section view of the hypodermic syringe with the needle during withdrawal of fluids.
Figure 14:
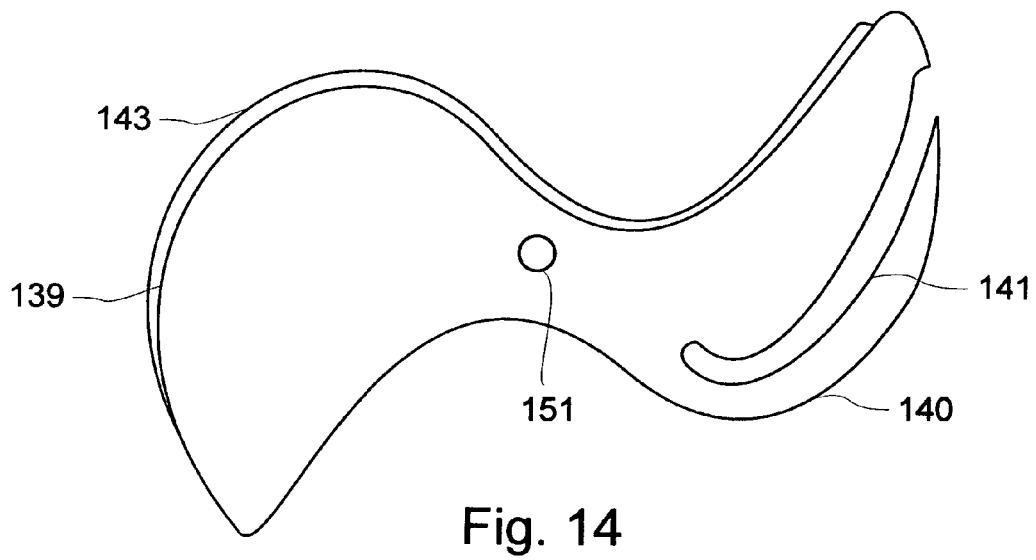
FIG. 14 is a view of the moving member with releasing plunger head extension guide.
Figure 15:
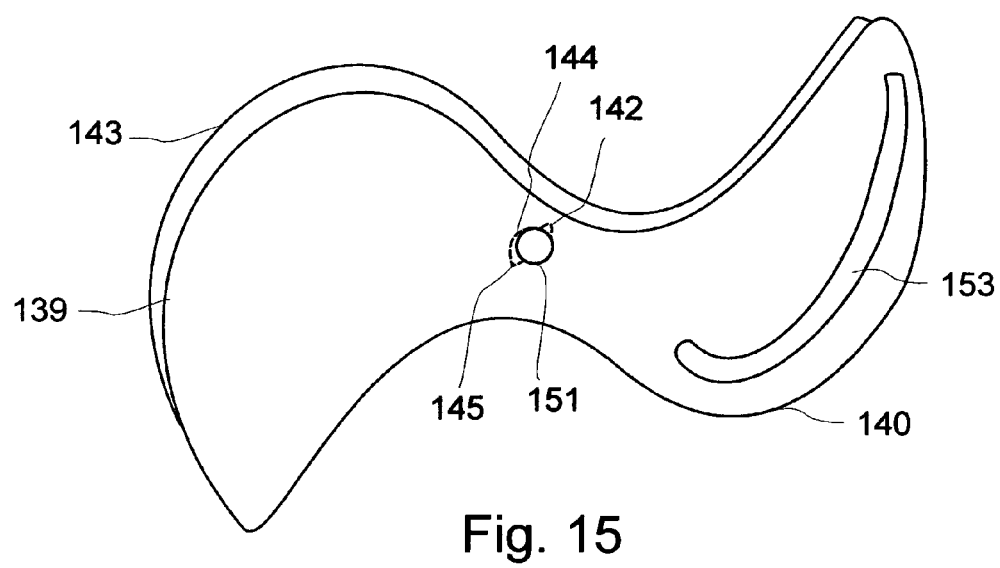
FIG. 15 is a view of the moving member with the non-releasing plunger head extension guide.

At least one moving member 131 is placed inside the syringe tube 102. Moving member 131 may be attached to the fulcrum point 115 on the syringe depression 114 as shown in FIG. 1 or placed between the syringe depression 114 and the syringe head 116, as shown in FIG. 8. The moving member 131 is a means of reversal of motion when pulled at the plunger head extension guide 141 by the plunger head extension 112 as shown in FIG. 6. FIG. 14 and FIG. 15 show that the moving member 131 comprises of moving member plunger head edge 140 and moving member blunting member edge 139 that are either straight, curved or a combination thereof. Moving member blunting member edge 139 pushes the blunting member 132 further into the needle member 118 to sheath the needle puncture tip 126. Moving member 131 has a blunting member guide 143 to guide the movement of the blunting member 132. Blunting member guide 143 is either flat, raised, depressed, textured, have gear teeth or a combination thereof, as a means of guiding blunting member 132. Moving member 131 has a plunger head extension guide 141 that is either flat, raised, cut-out, depressed or a combination thereof to guide the movement of moving member 131 when pulled by the plunger head extension 112. Moving member has an incline to facilitate assembly and movement in one direction. It has a stopper 142 to stop movement in one direction.

Plunger rod 104 extends into plunger head 110 flattened at one surface 111 aligned with the flat surface of the syringe tube 103. Plunger head 110 has a plunger head extension 112 that attaches or fastens to the moving member 131, pulls it with the pulling action of the plunger rod 104, and detaches after pushing the blunting member 132 further into the needle tube 121 to sheath the needle puncture tip 126, as shown in FIG. 7.

FIG. 16 to FIG. 19 show that the Releasing joint has two parts one being the releasing joint releasing part 146 and the other part being releasing joint released part 147. Either one of them can be on the moving member 131 and the other on the plunger head extension 112. Alternately releasing joint can be between multiple moving members 131 or between fulcrum point 115 and moving member 131. Releasing joint releasing part 146 is an arc and the releasing joint released part 147 is a segment of a circle. Segment is placed inside the arc in a position so that the longer width of the segment is aligned with the arc opening. Segment rotates in the arc until the point where the shorter width of the segment is aligned to the arc opening. At the point where the shorter width of the segment is aligned to the arc opening the segment is released from the arc.

Syringe tube 102, flattened plunger arm 106, plunger head 110, syringe head 116, needle mouth 119, and blunting member 132 have a flattened surface for alignment.

Figure 10:
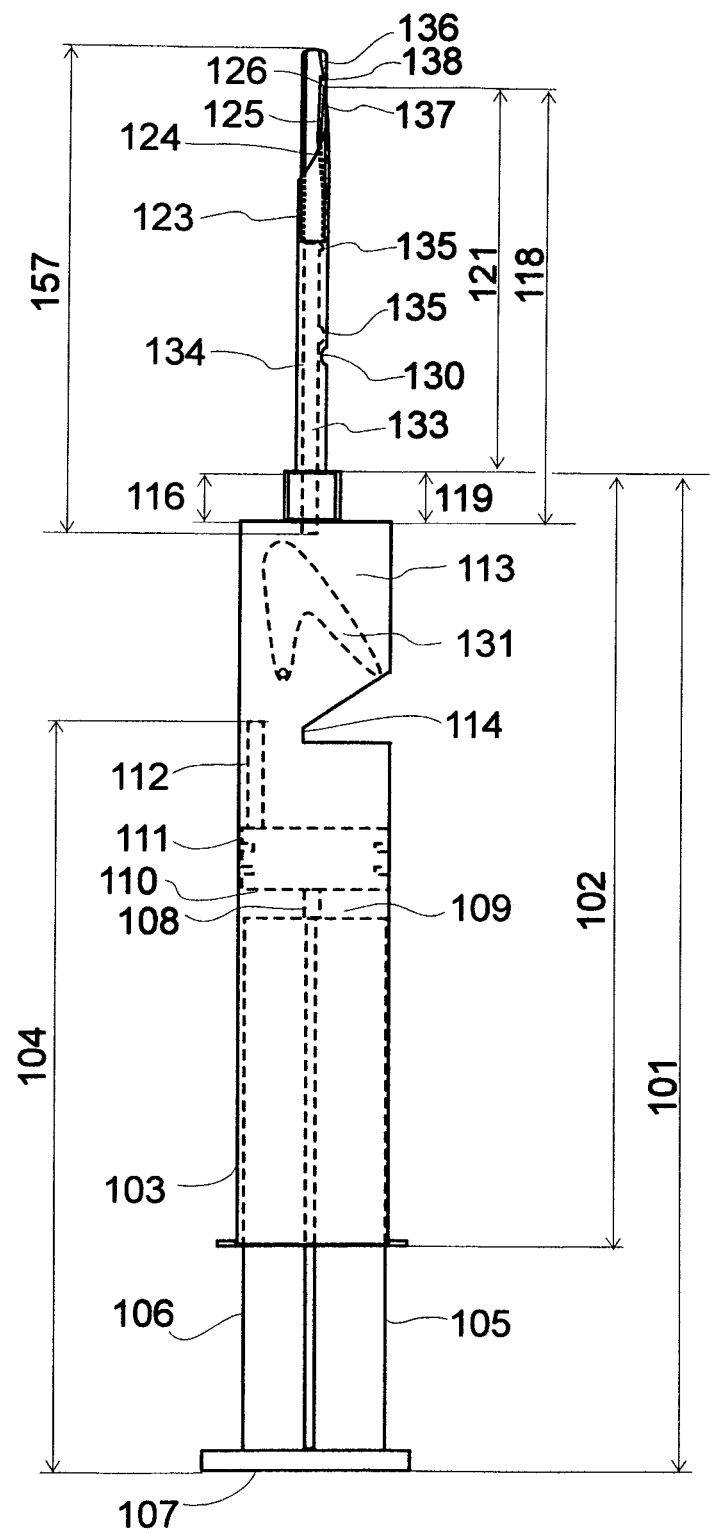
FIG. 10 is a view of the hypodermic syringe with needle with the moving member not attached to fulcrum point, after use.

FIG. 7 and FIG. 10 show that the pulling action of the plunger rod 104 pulls the plunger head 110 and plunger head extension 112, this moves the moving member 131. The movement of the moving member 131 pushes the blunting member 132 further into the needle tube 121, the blunting member 132 gets extended and the needle puncture tip 126 gets sheathed within the periphery of the blunting member 132.

FIG. 1 is a complete view of the needle system and syringe, showing a hypodermic syringe generally represented at 101 and syringe tube at 102. Unlike a typical tubular syringe, the syringe has a flattened surface along the syringe tube length represented at 103. The plunger rod is generally indicated at 104, the plunger rod shall have a normal plunger arm at 105 and a flattened plunger arm at 106, to align with the flattened surface of the syringe tube at 103. The plunger rod 104 has a thumb rest at 107.

The plunger arms extend into a plunger head support at 108. There is a cavity 109 between the plunger arms and the plunger head 110. The plunger head 110 has a flattened surface 111 to align with the flattened surface of the syringe tube 103. From the plunger head 110 emerges plunger head extension 112 into the syringe cavity 113. The plunger head extension 112 fastens or is attached to the moving member 131, pulls it with the pulling action of the plunger rod 104, and detaches after pushing the blunting member 132 further in to the needle tube 121 to sheath the needle puncture tip 126. Inside the syringe tube 102 there is a raised surface, syringe depression at 114 with fulcrum point 115. Syringe depression at 114 is represented in detail in FIG. 12.

Continuing with FIG. 1 syringe tube 102 extends into syringe head 116 and has a syringe head flattened surface 117 for alignment with needle mouth flattened surface 120 on needle mouth indicated at 119. Needle member is generally represented at 118.

Figure 11:
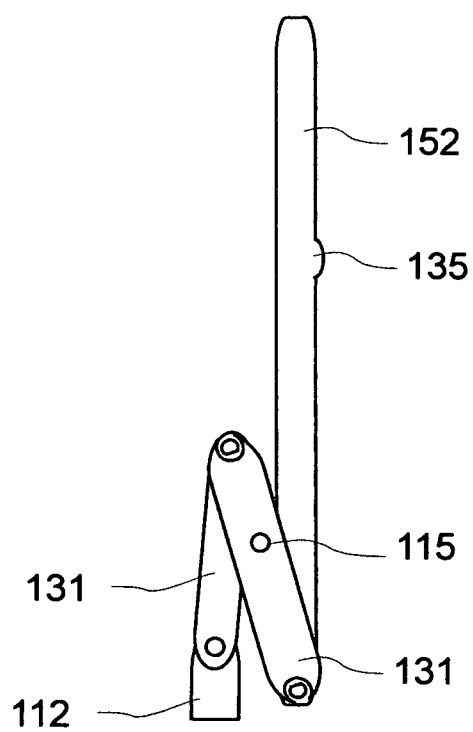
FIG. 11 shows multiple moving members.

FIG. 2 is a length wise cross section view of the needle consisting of the needle mouth 119, needle tube 121 and blunting member 132. The blunting member 132 is placed inside the needle tube 121. The blunting member 132 can comprise of a single part or be divided into multiple parts. Blunting member 132 may extend out side the needle mouth 119 into the syringe tube 102 or one of the parts of the blunting member 132 can extend outside the needle mouth 119 into the syringe tube 102 to be pushed by the moving member 131 or the moving member can have an extension 152 going into the needle tube 121 to push the blunting member 132 as shown in FIG. 11. The blunting member 132 can be of any shape as long as it aligns within the needle, to allow for the flow of fluids and locks. For the flow of fluids the needle tube 121 has a needle cavity 122 and the blunting member 132 has blunting member cavity 133. Instead of the typical tubular needle, the needle mouth 119, the needle tube 121 and the blunting member 132 have a flattened surface along the length at 120, 123, and 134 respectively, to allow for alignment. Needle tube 121 has a needle opening at 124 and needle curvature at 125.

The needle mouth 119 when affixed to the syringe head 116, brings the blunting member 132 in alignment with the plunger head extension 112. The needle puncture tip 126 has a small inward or outward curvature at 125. The needle puncture tip 126 extends upward at an acute angle at needle tip angle 127. The blunting member 132 has two indents. The first indent 136 allows for the blunting member to smoothly glide over the needle curvature 125.

Figure 3:
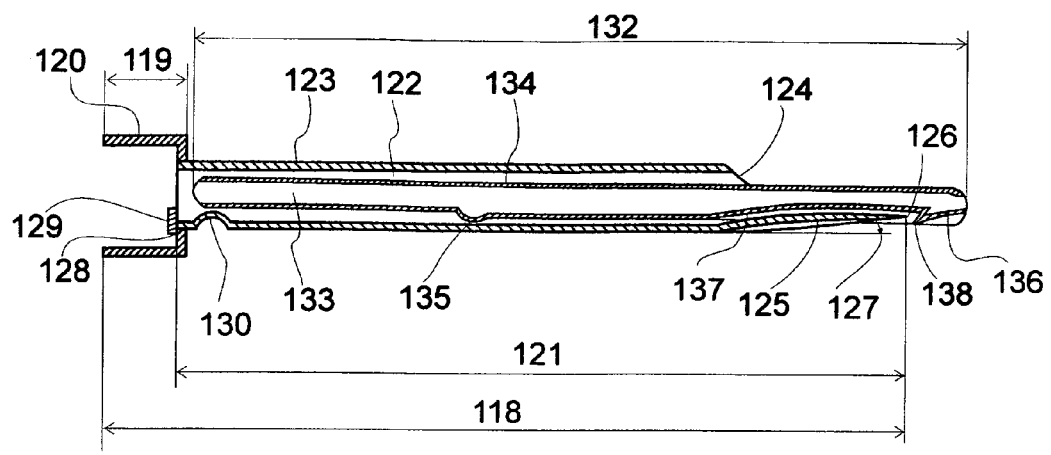
FIG. 3 is the cross section view of the needle during after withdrawal of fluids.

The sheathing indent 137 is curved to correspond with the curvature in the needle 125. FIG. 3 shows the blunting member 132 is completely extended the sheathing indent 137 will sheath the needle puncture tip 126 of the needle generally represented at 118. The needle puncture tip 126 of the needle is covered by the puncture tip protector 138. The blunting member has a curvature 135 that stops the blunting member 132 or its multiple parts from falling out of the needle mouth 119, when it is stopped by the blunting member stopper 129 or the alternate blunting member stopper 130 on the needle member. Blunting member stopper 129 is placed where the needle mouth and needle tube touch 128.

The blunting member 132 can be of any shape or there may be transition of shape which allows for the free flow of fluids as shown in FIG. 4. The aim of the aforementioned shapes is alignment, flow of fluids and locking with the needle tube 121. Alternately to the blunting member curvature 135 the blunting member 132 has a variation in thickness 154, where the thicker part gets stopped at either the blunting member stopper 129 or alternate blunting member stopper 130 on the needle member 118. It also shows the blunting member with transition of shape 156.

Figure 5:
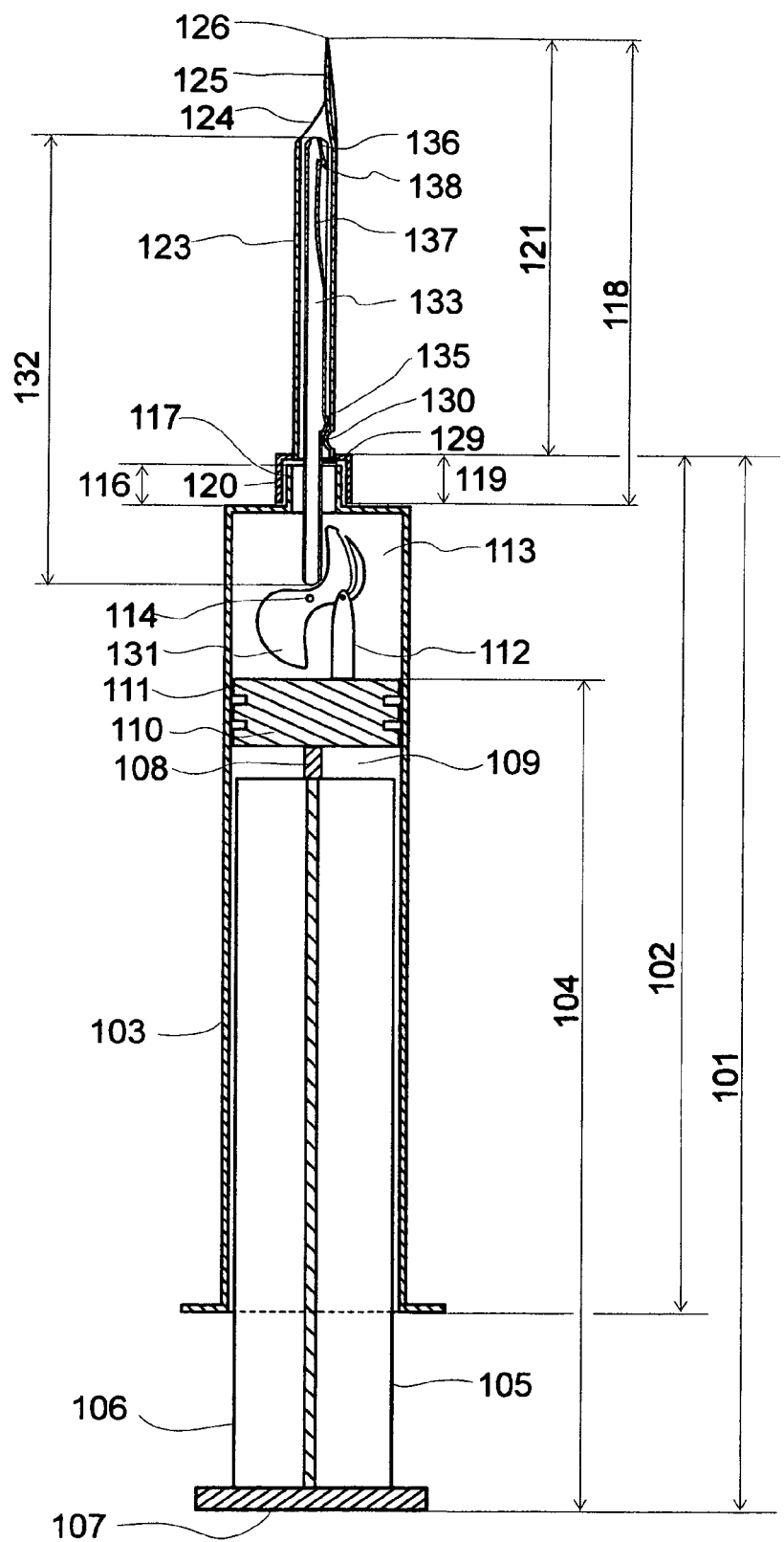
FIG. 5 is the cross section view of the hypodermic syringe with the needle in shipping position.

FIG. 5 is the cross section view of the syringe & needle in shipping position. FIG. 6 shows that with the intake of fluids the plunger rod 104 is pulled outward of the syringe tube 102. This action of pulling further pulls the moving member 131. Plunger head 110 may be connected to the moving member 131 directly or with a plunger head extension 111. With the pulling action of the plunger rod 104, the plunger head 110 or the plunger head extension 112 pulls the moving member 131, movement of the moving member 131 is a means of reversal of motion. The pulling action of the moving member 131 pushes the blunting member 132 further into the needle tube 121. The blunting member 132 extends to sheath the needle puncture tip 126 within the periphery of the blunting member 132.

FIG. 7 represents the syringe and needle after use, where the moving member 131 is released from the plunger head extension 112 and the needle puncture tip 126 remains sheathed by the blunting member 132.

There is at least one moving member 131 placed inside the syringe tube 102. Moving member 131 is fastened or attached to the fulcrum point 115 on the syringe depression 114. FIG. 8 shows an alternative where the moving member 131 is placed between the syringe depression 114 and syringe head 116. The figure also shows multiple blunting members at 157. FIG. 9 shows the moving member 131 placed between the syringe depression 114 and syringe head 116 during the withdrawal of fluids. The action of pulling of the plunger head extension 112 with the plunger rod 104 moves the moving member 131. The syringe depression 114 guides movement of the moving member 131. The figure also shows multiple blunting members at 157. FIG. 10 shows that after pushing the blunting member 132 further into the needle tube 121 to sheath the needle puncture tip 126, the moving member 131 is released from the plunger head extension 112 as the syringe depression 114 stops the movement of the moving member 131 in one direction. The needle puncture tip 126 remains sheathed with the blunting member 132. The figure also shows multiple blunting members at 157.

FIG. 11 shows an alternate option of the moving member extension 152 which pushes the blunting member 132 placed inside the needle tube 121. This figure also shows multiple moving members 131.

FIG. 12 represents the cross section of the syringe depression 114. A raised member inside the syringe tube 102 is independently or in combination is means of providing a fulcrum point, guide movement and stop movement of moving member 131 in a direction.

Figure 13:
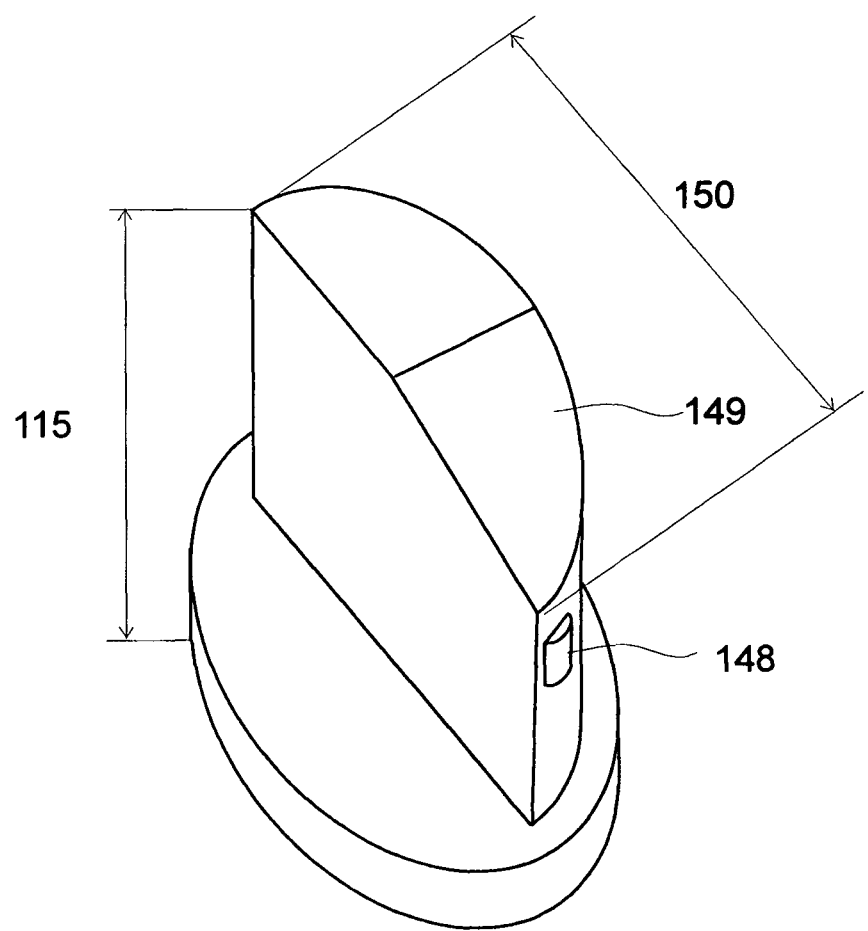
FIG. 13 is a view of the fulcrum point.

FIG. 13 shows fulcrum point 115 on the syringe depression 114. Fulcrum point provides a pivot for moving member 131. Pivot point is a point about which things turn. Fulcrum point 115 also stops movement of the moving member 131 in one direction. Fulcrum point 115 has a means of attachment and fastening to provide ease of assembly with the moving member 131. Moving member 131 stays attached to the fulcrum point 115 or alternately the fulcrum point 115 allows the release of the moving member 131 after pushing the blunting member 132 further into the needle tube 121 to sheath the needle puncture tip 126. Fulcrum point 115 has a fulcrum point stopper 148 to stop movement in a direction. Fulcrum point 115 has a fulcrum point incline 149 for ease of assembly and release. Fulcrum point 115 has a released part 150 that gets released from the moving member fulcrum joint 151.

FIG. 14 shows the moving member 131 that is a means of reversal of motion when pulled at the plunger head extension guide 141 by the plunger head extension 112 or the plunger head 110. This figure shows the moving member 131 with the releasing plunger head extension guide 141.

The moving member 131 comprises of moving member plunger head edge 140 and moving member blunting member edge 139 that are either straight, curved or a combination thereof. Moving member's blunting member edge 139 pushes the blunting member 132 further into the needle tube 121 to sheath the needle puncture tip 126.

Moving member 131 has a blunting member guide 143 to guide the movement of blunting member 132. Blunting member guide 143 is either flat, raised, depressed, textured, have gear teeth or a combination thereof, as a means of guiding the blunting member 132.

Moving member 131 has a plunger head extension guide 141 that is either flat, raised, cut-out, depressed or a combination thereof to guide the movement of moving member 131 when pulled by the plunger head 110 or plunger head extension 112.

Moving member 131 has an incline to facilitate assembly and movement in one direction. The moving member incline has a lower part 144 and higher part 145. Moving member has a stopper 142 to stop movement in one direction. Moving member has a moving member fulcrum joint 151 which attaches or fastens to the fulcrum point 115.

FIG. 15 shows the moving member 131 with the non-releasing plunger head extension guide 153 by having an enclosed guide.

Figure 16:
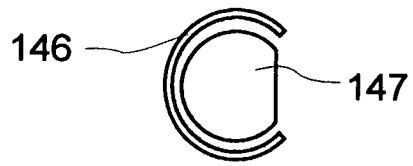
FIG. 16 is the releasing joint with segment placed inside the arc so that the longer width of the segment is aligned with the arc opening.
Figure 17:
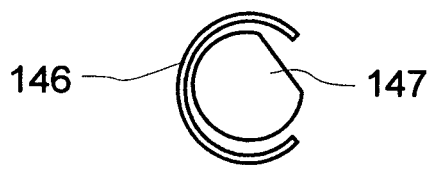
FIG. 17 is the releasing joint with the segment and arc position during movement.
Figure 18:
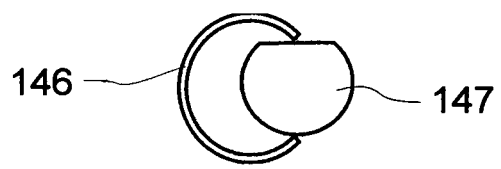
FIG. 18 is the releasing joint where the shorter width of the segment is aligned to the arc opening.
Figure 19:
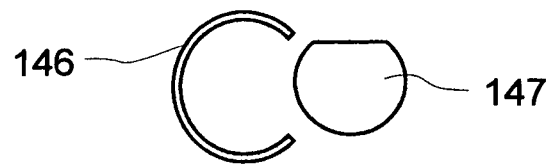
FIG. 19 is the releasing joint where the released part is released.

Releasing joint has two parts one being the releasing joint releasing part and the other part being the releasing joint released part. Either one of them can be on the moving member 131 or the other on the plunger head extension 112. Releasing joint is also used when there are multiple moving members as shown in FIG. 11. Releasing joint releasing part 146 is an arc and the releasing joint released part 147 is a segment of a circle. FIG. 16 shows the segment releasing joint released part 147 is placed inside the arc releasing joint releasing part 146 in a position so that the longer width of the segment releasing joint released part 147 is aligned with the arc releasing joint releasing part 146 opening. FIG. 17 shows the releasing joint during movement. FIG. 18 shows the segment releasing joint released part 147 has rotated in the arc releasing joint releasing part 146 until the point where the shorter width of the segment releasing joint released part 147 is aligned to the arc releasing joint releasing part 146 opening. FIG. 19 shows when the arc releasing joint releasing part 146 and the segment releasing joint released part 147 are released.

Figure 20:
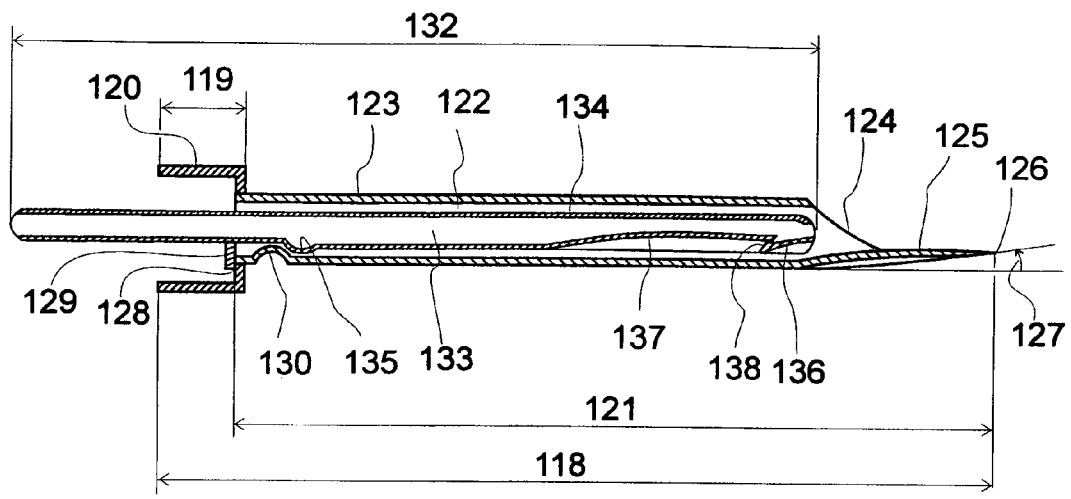
FIG. 20 shows cross section of blunting member and needle with inward curvature and needle tip at angle.

FIG. 20 is a cross section view of the needle and the blunting instrument with two inward curvatures at 136 and 137 in shipping position. The puncture tip of the needle is at an angle 127. After withdrawal of the fluid, the sheathing indent 137 sheaths the needle puncture tip 126, the puncture tip protector 138 covers the tip and gets locked in place.

Figure 21:
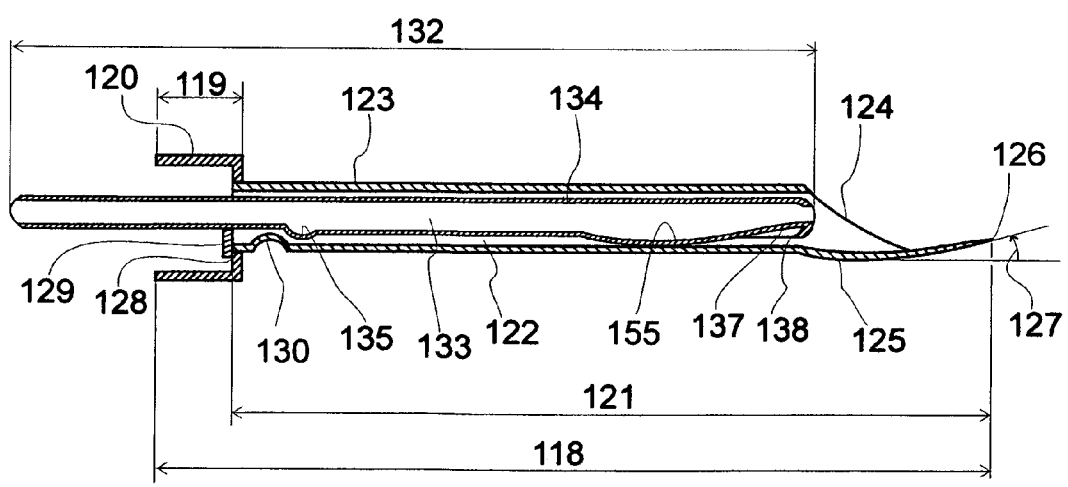
FIG. 21 shows cross section of blunting member and needle with outward curvature and needle tip at angle.

FIG. 21 is a length wise cross section view of the needle with curvature 125 that is outward and the blunting member 132 with an outward indent 155 at shipping position. The blunting member has an outward indent at 155 and an inward sheathing indent at 137 which juts out to form puncture tip protector at 138. The puncture tip of the needle is at an angle 127. After withdrawal of the fluid, the outward indent 155 gets locked at the needle curvature 125 and the needle puncture tip 126 is covered by the puncture tip protector 138.

Figure 22:
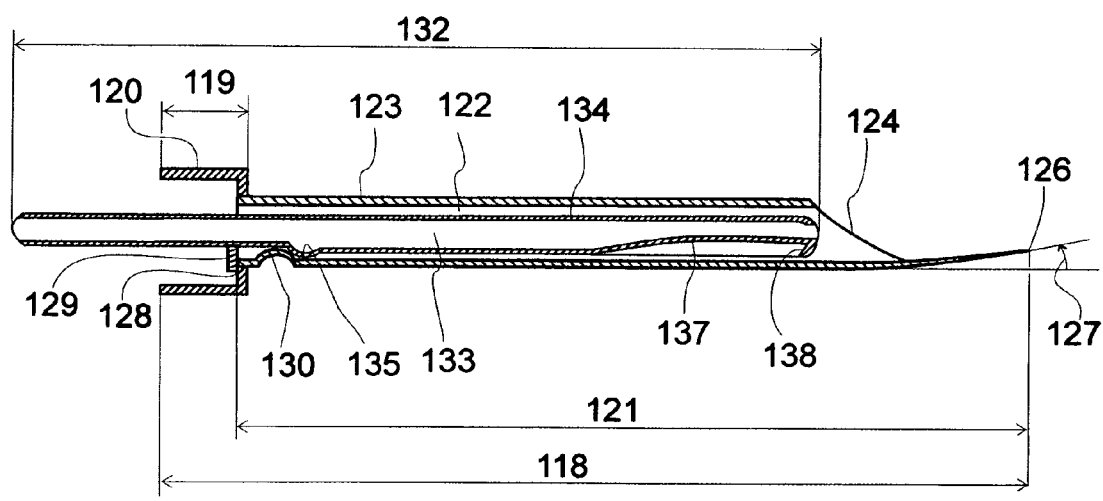
FIG. 22 shows cross section of blunting member and needle wherein the needle tip is at an angle.

FIG. 22 shows cross section of blunting member 132 and needle 118 wherein the needle tip is at an angle 127. The blunting member one sheathing indent 137 and a needle tip protector 138. Blunting member has a curvature 135.

Figure 23:
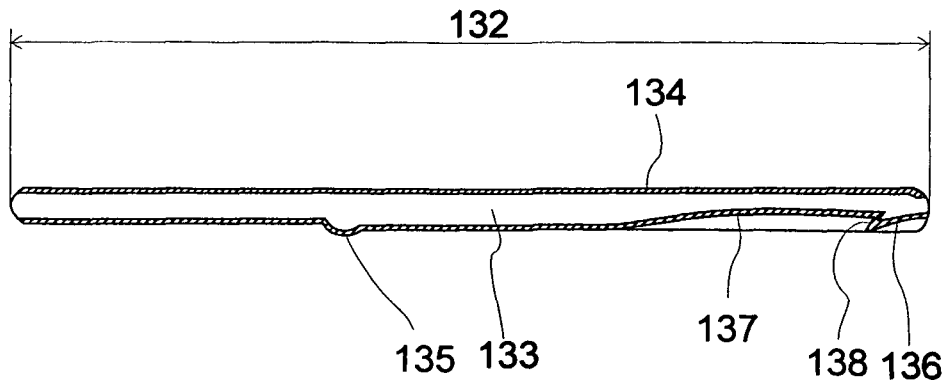
FIG. 23 shows cross section view of blunting member with two inward curvatures.

FIG. 23 is a cross section view of the blunting instrument with two inward curvatures at 136 and 137. The puncture tip protector is represented at 138. Blunting member has a curvature 135.

Figure 24:
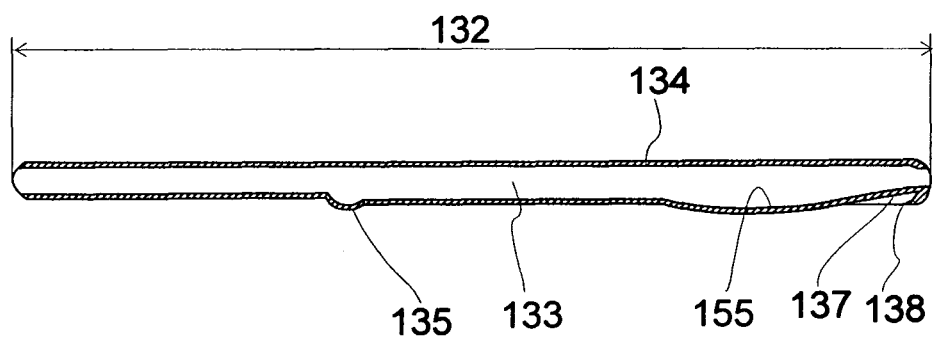
FIG. 24 shows cross section view of blunting member with one outward curvature and one inward curvature.

FIG. 24 is a length wise cross section view of the blunting member 132 with an outward indent 155. The Blunting member 132 has an outward indent at 155 and an inward sheathing indent at 137 which juts out to form puncture tip protector at 138. Blunting member has a curvature 135.

Figure 25:
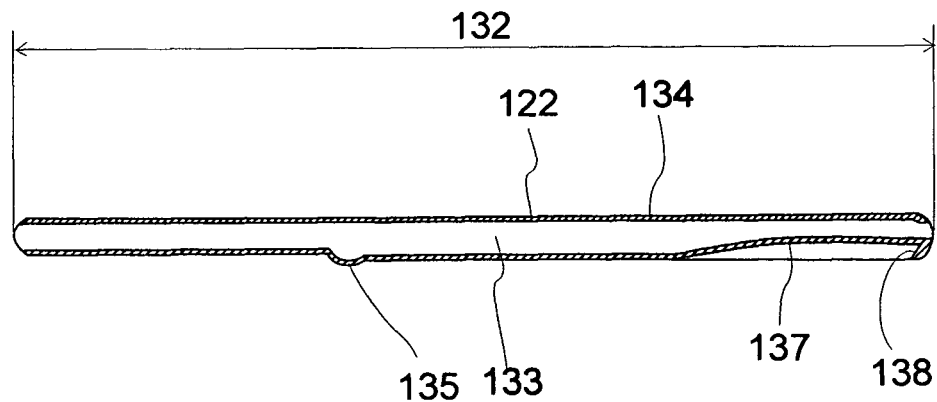
FIG. 25 shows cross section view of blunting member with one inward curvature.

FIG. 25 shows cross section of blunting member 132 wherein the blunting member has one sheathing indent 137, a needle tip protector 138 and a curvature 135.

While the above description contains much specificity, these should not be construed as limitations on the scope of the invention, but as exemplifications of the presently preferred embodiments thereof. Many other ramifications and variations are possible within the teachings of the example. Thus the scope of the invention should be determined by the appended claims and their legal equivalents, and not only by the examples given.

Sequence Listing

Not applicable

The present invention has been made to protect the health of medical and non-medical persons who face the risk of needle stick injury . . . Devices of this invention may be employed to extract or expel fluids or gasses for both medical and non-medical purposes.

I claim:

1. A self locking and self blunting safety syringe comprising:
    a needle assembly comprising:
        a needle tube,
        a needle puncture tip, and
        a blunting member placed in the needle tube; and
    a syringe assembly comprising:
        a syringe tube,
        a plunger rod, and
        a moving member;
    wherein backward pulling action of said plunger rod pulls said moving member to rotate said moving member about an axis perpendicular to a longitudinal axis of said safety syringe, and wherein rotation of said moving member pushes forward said blunting member inside said needle tube distally past said needle puncture tip to sheathe and lock said needle puncture tip from inside said needle tube.

2. The safety syringe of claim 1, wherein said plunger rod has a plunger head attached to said moving member to guide movement of said blunting member into said needle tube, and after pushing said blunting member into said needle tube, said plunger head releases said moving member.

3. The safety syringe of claim 2, wherein said plunger head has a plunger head extension attached to said moving member to guide movement of said blunting member forward into said needle tube, and after pushing said blunting member forward into said needle tube, said plunger head extension releases said moving member.

4. The safety syringe of claim 1, wherein said needle tube has an alternate blunting member stopper to stop said blunting member and parts thereof from falling out of a needle mouth while allowing movement in forward direction towards said needle puncture tip.

5. The safety syringe of claim 1, wherein said blunting member and parts thereof provide alignment to move inside said needle tube while allowing fluid flow of fluids inside said needle tube.

6. The safety syringe of claim 1, wherein said blunting member has a blunting member curvature to stop said blunting member and parts thereof from falling out of a needle mouth while allowing movement in said forward direction towards said needle puncture tip.

7. The safety syringe of claim 1, wherein said blunting member has a variation in thickness to stop said blunting member and parts thereof from falling out of a needle mouth while allowing forward movement towards said needle puncture tip.

8. The safety syringe of claim 1, wherein said blunting member placed inside said needle tube extends into said syringe tube to allow said blunting member being pushed by said moving member.

9. The safety syringe of claim 3, wherein said moving member allows reversal of direction of motion by backward pulling action of: said plunger head; and said plunger head extension.

10. The safety syringe of claim 1, wherein:
    said moving member is placed inside said syringe tube;
    said moving member has a moving member blunting member edge and a moving member plunger head edge;
    said moving member is attached to a fulcrum point on a syringe depression; and
    said moving member is alternately placed between said syringe depression and a syringe head.

11. The safety syringe of claim 1, wherein said moving member has a moving member extension going into said needle tube to push said blunting member forward toward said needle puncture tip.

12. The safety syringe of claim 3, wherein said moving member has a plunger head extension guide on said moving member that:
    allows attachment to said plunger head extension;
    allows being pulled by said plunger head extension;
    guides movement of said moving member when pulled;
    allows detachment from said plunger head extension;
    allows attachment to said plunger head;
    allows being pulled by said plunger head;
    guides movement of said moving member when pulled by said plunger head; and
    allows detachment from said plunger head.

13. The safety syringe of claim 10, wherein said moving member has said moving member blunting member edge to push said blunting member.

14. The safety syringe of claim 13, wherein said moving member blunting member edge guides said blunting member and parts thereof.

15. The safety syringe of claim 1, wherein said moving member has an incline to guide movement direction of said plunger rod.

16. The safety syringe of claim 1, wherein said moving member has a moving member stopper to guide movement and direction.

17. The safety syringe of claim 1, wherein said syringe tube has a syringe depression that is a raised member inside said syringe tube to provide: position for a fulcrum point; guiding movement of said moving member; and to limit excess movement of said moving member.

18. The safety syringe of claim 17, wherein said fulcrum point on said syringe depression: provides a pivot point for said moving member; guides movement of said moving member; guides direction of said moving member; attaches to said moving member; and releases said moving member.

19. The safety syringe of claim 1, further comprising a releasing joint which joins parts inside said syringe tube to other parts and comprises:
    a releasing joint released part, and
    a releasing joint releasing part; and
    wherein said releasing joint releasing part releases said releasing joint released after required movement.

20. The safety syringe of claim 1, wherein backward pulling action of said plunger rod pushes said blunting member forward to sheathe and lock said needle tip during intake of fluids.

\* \* \* \* \*